United States Patent [19]

Hasson

[11] 3,971,384
[45] July 27, 1976

[54] SURGICAL CLOSURE
[76] Inventor: Harrith M. Hasson, 6942 N. Waukesha Ave., Chicago, Ill. 60646
[22] Filed: Dec. 17, 1971
[21] Appl. No.: 209,165

Related U.S. Application Data
[63] Continuation-in-part of Ser. No. 123,559, March 12, 1971, Pat. No. 3,698,395.

[52] U.S. Cl. .............................................. 128/335
[51] Int. Cl.² ........................................ A61B 17/08
[58] Field of Search .................. 128/335, 334, 337; 24/16 PB, 20 TT, 16 R, 20 R, DIG. 23, 30.5 PB, 203, 206 R

[56] References Cited
UNITED STATES PATENTS
2,223,006  11/1940  Laub .................................. 128/335
2,798,492  7/1957  Barnes ............................... 128/335
3,118,201  1/1964  Beghetto ........................... 24/16 R Primary Examiner—Robert W. Michell
Assistant Examiner—Lee S. Cohen
Attorney, Agent, or Firm—Norman Lettvin

[57] ABSTRACT

A sutureless closure device which is operable to draw the edges of a wound or incision together. The device comprises two pieces of surgical tape each having an adhesive face. These pieces are secured to the skin on opposite sides of the incision. An anchor for one end of a tie strip is carried by the exposed face of one tape. A slide is secured to the exposed face of the other tape. A tie strip having ratchet teeth on its upper or exposed face has one end secured to the anchor with its other end being taken up in the slide. The slide includes a locking tab which secures the tie strip by cooperating with the ratchet teeth thereon after the tie strip has been drawn to a desired degree of tautness.

7 Claims, 6 Drawing Figures

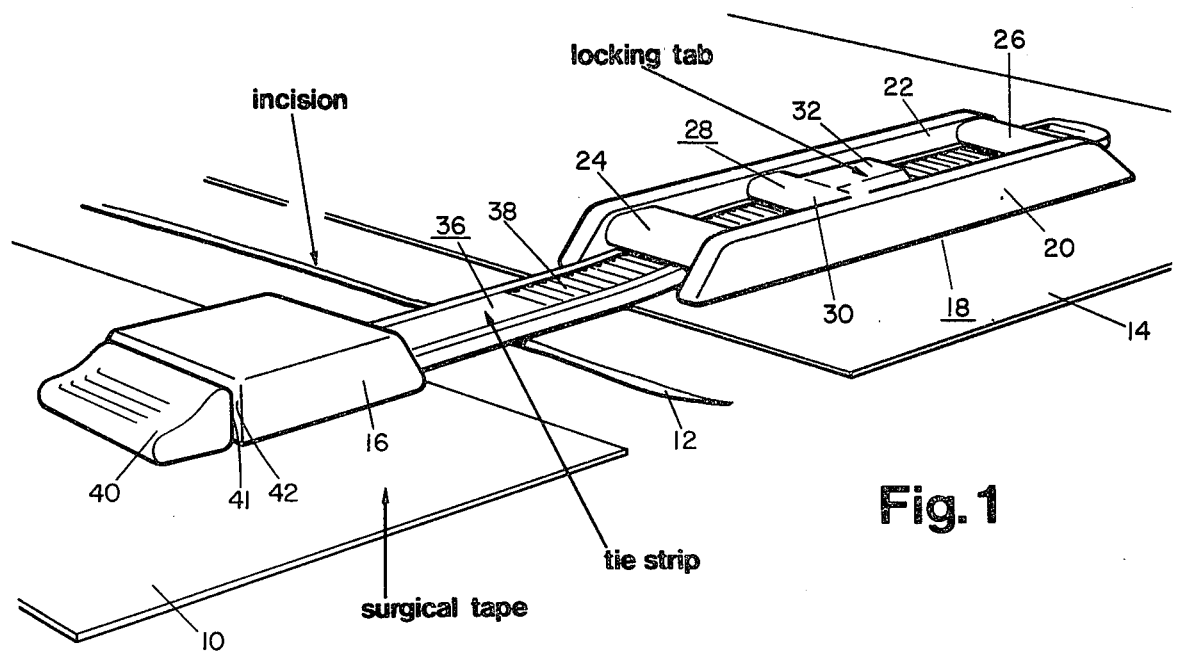
Fig. 1
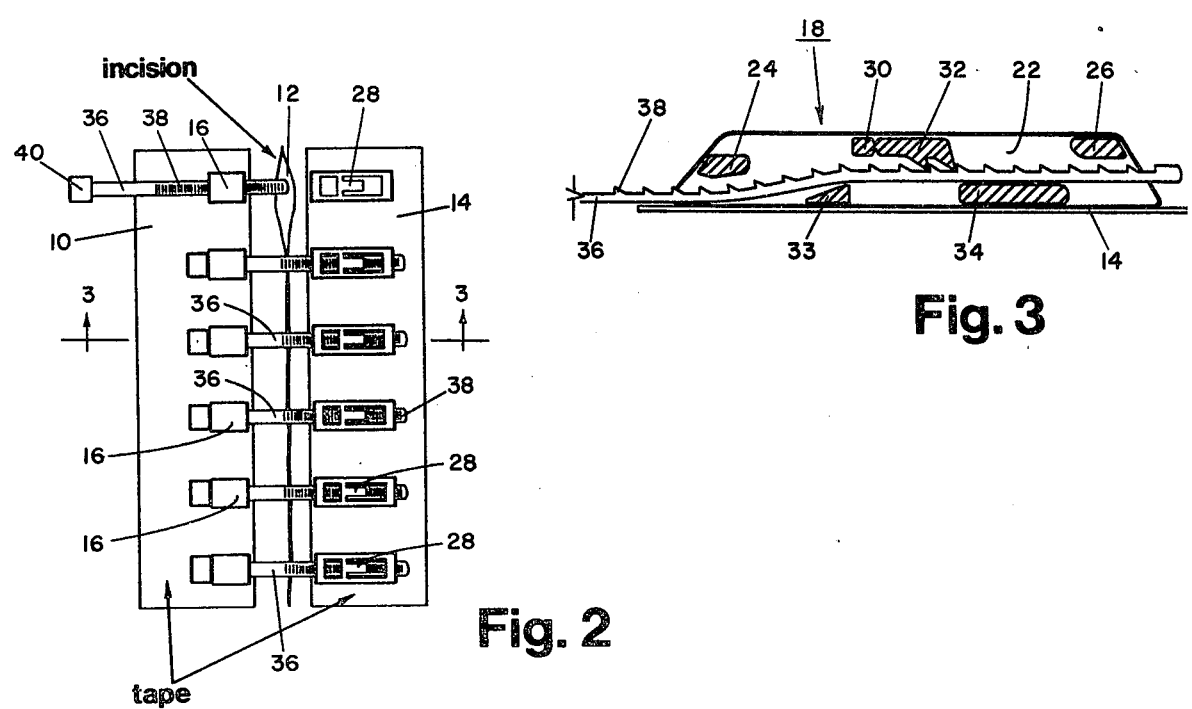
Fig. 2
Fig. 3

SURGICAL CLOSURE

This application is a continuation-in-part of my application Ser. No. 123,559, filed Mar. 12, 1971, now U.S. Pat. No. 3,698,395.

BACKGROUND OF THE INVENTION

This invention relates to a novel surgical closure device which overcomes many of the obstacles and deficiencies of prior art sutures.

One very widely used prior art surgical technique is the suture or clip technique which comprises stitching or applying clips to the incision in order to close it, and requires subsequent removal of the stitches or clips. However, the suture or clip technique has several disadvantages. Often the needle or the clips will go through a blood vessel causing bleeding. Further, closing the incision by means of sutures or clips has been found to be very time consuming. Additionally, the removal of sutures or clips after several days causes added discomfort, inconvenience, and such sutures or clips normally leave scars. An example of a prior art suture device is disclosed in the patent to Lemole, U.S. Pat. No. 3,570,497, and an example of a prior art clip device is disclosed in the patent to LeRoy, U.S. Pat. No. 3,385,299.

Other surgical closures, which do not require stitching or applying clips to the incision, have been described. For example, in the patent to Penny, U.S. Pat. No. 363,538, issued May 24, 1887, a closure device utilizing a rubber band coupling member is disclosed. However, such rubber bands are subject to breakage and Penny's surgical closure lacks adjustability, an important ingredient in an effective surgical closure. In the patent to Demuth, U.S. Pat. No. 2,012,755, issued Aug. 27, 1935, a surgical closure is provided utilizing a zipper device. However, this surgical closure also lacks adjustability. Adjustability is provided in the surgical closure of the patent to Radcliffe, U.S. Pat. No. 1,428,495, issued Sept. 5, 1922. However, Radcliffe's surgical closure requires stitching which has been found to be very time consuming.

Another method used to close small wounds is the application of separate narrow adhesive strips, such as "Steri-Strips", manufactured by 3M Company, to opposing skin edges. Such narrow adhesive strips can only be used on very small wounds because the closure tends to loosen and come apart with stress.

It is, therefore, an object of the present invention to provide a surgical closure which obviates the need for applying clips or sewing incisions closed, thus minimizing scar formation.

It is another object of the present invention to provide a surgical closure which enables a surgeon to close an incision in a rapid, effective manner, without having to puncture the skin, thereby removing the possibility of bleeding caused by the closure.

A further object of the present invention is to provide a surgical closure which does not require the use of stitches, or sutures, and which allows a surgeon to selectively provide the proper amount of closure tension on the incision.

Other objects and advantages will become apparent from the following description, claims, and the illustrations in the drawing.

BRIEF DESCRIPTION OF THE INVENTION

In accordance with the present invention, there is provided a surgical closure comprising a first surgical tape member for application to one side of an incision and a second surgical tape member for application to the other side of the incision. As used in the specification and claims, the term "incision" encompasses all types of skin cuts, including wounds and surgical incisions.

The first surgical tape member carries a tie strip anchor and the second surgical tape member carries a tie strip slide which includes a releasable locking member. A tie strip is provided for coupling the second surgical tape members, with the tie strip having means for engaging the anchor.

In the illustrative embodiment of the invention, the tie strip has a toothed upper surface to form a ratchet, and the locking member comprises a pawl. The tie strip is an independent element adapted for connection to the anchor and tie strip slide by an operator at the time the incision is to be closed.

A more detailed explanation of the invention is provided in the following description and claims, and is illustrated in the accompanying drawing.

BRIEF DESCRIPTION OF THE DRAWING

FIG. 1 is a fragmentary, perspective view of a closure device in accordance with the principles of the present invention;

FIG. 2 is a top plan view thereof, showing a number of the tie strips connected to close a portion of the incision and further showing one of the tie strips about to be so connected;

FIG. 3 is a cross-sectional view of the slider of the closure device of FIG. 2, taken along the line 3—3 of FIG. 2;

DETAILED DESCRIPTION OF THE ILLUSTRATIVE EMBODIMENTS

Figure 4:
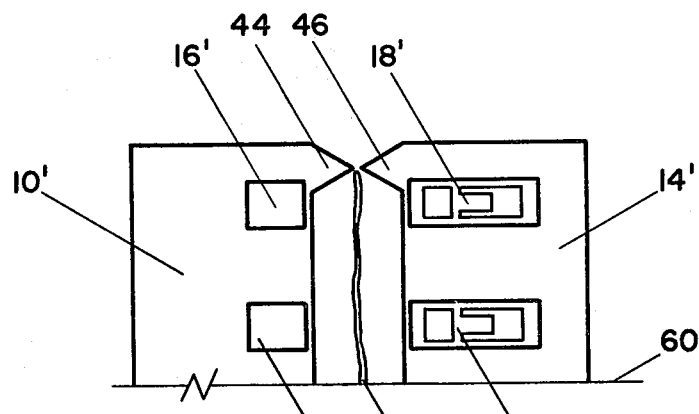
FIG. 4 is a diagrammatic view of a closure device in accordance with a second form of the invention.

Referring to FIGS. 1 and 2, it can be seen that a first piece of flexible surgical tape 10 having a pressure sensitive adhesive undersurface is applied to the skin on one side of incision 12 while a second flexible piece of surgical tape 14 having a pressure sensitive adhesive undersurface is applied to the other side of incision 12. Tape 10 has fastened to it an anchor 16, preferably formed of plastic in a hollowed, rectilinear configuration, and tape 14 has affixed to it a slide 18, preferably formed of plastic and comprising parallel sides 20, 22 which are bridged by plastic cross members 24, 26. A locking tab 28 having a pivotal portion 30 bridging sides 20 and 22 is provided and forms a pawl with its free portion 32 forming the active member of the pawl. Slide 18 also contains lower members 33, 34 which bridge sides 20 and 22 and support a belt-like tie strip 36. Tie strip 36 is preferably formed of a flexible plastic material having teeth 38 formed on its upper surface to provide a ratchet for engagement with locking tab 28. A finger-pressing member 40 having stop means 41 is affixed to one end of tie strip 36 for engagement with the end 42 of anchor 16. It can readily be seen that after tape pieces 10 and 14 are applied to the skin on opposite sides of the incision, tie strip 36 is inserted into and through anchor 16 and into and through slide 18. Thumb pressure is applied against member 40 and the skin on opposite sides of the incision is brought closer together until the incision is closed to a satisfactory degree. Locking tab 28 will cooperate with teeth 38 of the tie strip 36 to lock it in the manner illustrated in FIG. 3. The lower members 33, 34 hold the tie strip firmly against locking tab 28 to insure safe, positive locking. When desired, locking tab 28 may be disengaged from tie strip 36 to allow the tie strip to be loosened or removed. Such disengagement is performed with a suitable pointed tool.

Bridge 24 holds a portion of tie strip 36 flat against the skin for precise vertical apposition of the skin edges. Members 24 and 33 cooperate to force the tie strip into a generally S-shape which aids in this respect. The free end of the tie strip is restrained by member 26 to prevent accidental disruption of the locking engagement.

It is, of course, important that the closure be properly aligned with respect to the incision and that each of the pieces of surgical tape 10, 14 is substantially equally spaced from the incision. To this end, as illustrated in FIG. 4, surgical tape 10' which carries anchors 16' includes an aligning pointer 44 which extends and points towards an aligning pointer 46 formed integrally with surgical tape 14'. The tips of pointers 44 and 46 are spaced a short distance from each other to permit such spacing to overlie the incision thereby equally spacing the surgical tapes 10' and 14' from the incision.

Figure 5:
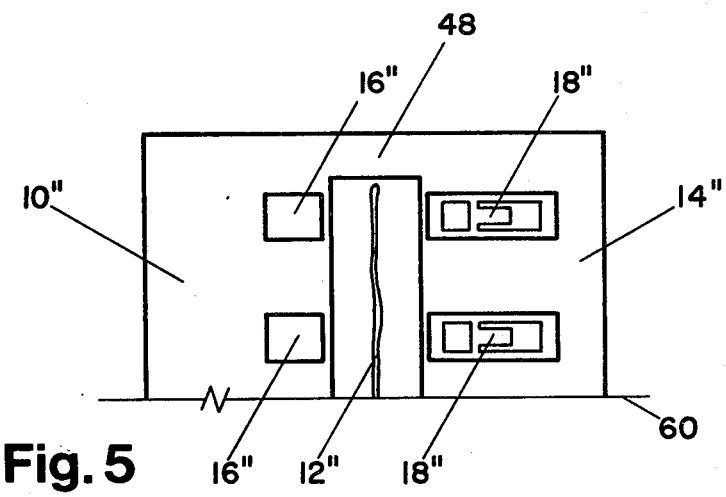
FIG. 5 is a diagrammatic view of a closure device in accordance with a third form of the invention.
Figure 6:
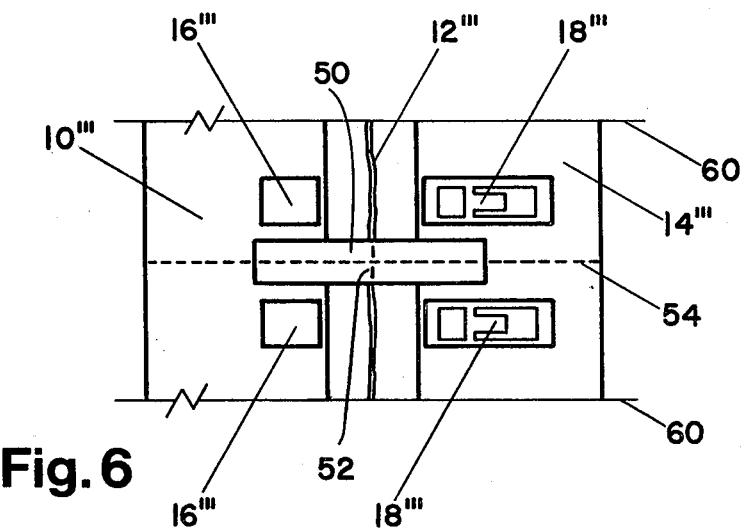
FIG. 6 is a diagrammatic view of a closure device in accordance with a fourth form of the invention.

Proper alignment of the tapes 10 and 14 with respect to the incision is achieved by utilizing aligning strips, such as shown in FIGS. 5 and 6. Referring to FIG. 5, it is seen that tapes 10'' and 14'' are bridged by integrally formed aligning strip 48, also formed of surgical tape. Strip 48 helps maintain the tapes 10'' and 14'' in proper relationship to each other and with respect to the incision 12''.

In FIG. 6, the aligning strip 50 takes the form of a separate tape member which bridges tapes 10'' and 14'' and is non-adhesive at the portion that will be in contact with the skin. This is in contrast to strip 48 of the FIG. 5 embodiment, which is adhesive and should be located away from the incision. Strip 50 is affixed to both tapes 10'' and 14'' and is formed of a transparent or translucent plastic material so that the incision can be viewed through the strip. A vertical indicator 52 is provided for aiding the alignment of the closure with respect to the incision. Tapes 10''' and 14''' and strip 50 include a perforated continuous tear line 54 for separating the desired amount of closure from a long roll. In using the FIG. 6 device, after the closure is applied to the skin, strip 50 is removed and tie strips 36 are thereafter inserted into anchors 16''' and slides 18'''.

Reference mumeral 60 in FIGS. 4, 5 and 6 indicates a possible severance line which may be at various locations so as to include one, two, three or more anchors and corresponding slides. It can be seen that the closure that is used could have any number of corresponding anchors and slides and could be severed from a long roll or the like.

It should be noted that similar reference numerals are used throughout the specification and drawings to indicate similar structure; however, one or more "primes" are added where different forms of the invention are presented.

Although several illustrative embodiments of the invention have been shown and described, it is to be understood that various modifications and substitutions may be made by those skilled in the art without departing from the novel spirit and scope of the present invention.

What is claimed is:

1. A surgical closure which comprises: a first surgical tape member for application to one side of an incision; a second surgical tape member for application to the other side of the incision; said first surgical tape member carrying a tie strip anchor and said second surgical tape member carrying a tie strip slide, said tie strip slide defining a slot to receive a tie strip and including a locking member; and a tie strip for sliding through said tie strip slide for coupling said first and second surgical tape members; at least a portion of said locking member being spaced, from the surface on which the tie strip lies, a distance that is smaller than the thickness of the tie strip, whereby said locking member can cooperate with said tie strip to maintain said tie strip within said tie strip slide; and further including a plurality of said surgical closures in a connected assembly, said connected assembly comprising tear strip means separating each surgical closure.

2. A surgical closure which comprises: a first surgical tape member for application to one side of an incision; a second surgical tape member for application to the other side of the incision; said first surgical tape member carrying a tie strip anchor and said second surgical tape member carrying a tie strip slide, said tie strip slide defining a slot to receive a tie strip and including a locking member; and a tie strip for sliding through said tie strip for coupling said first and second surgical tape members; at least a portion of said locking member being spaced, from the surface on which the tie strip lies, a distance that is smaller than the thickness of the tie strip, whereby said locking member can cooperate with said tie strip to maintain said tie strip within said tie strip slide; and further including means bridging said first and second surgical tape members for aiding the operator to align said tape members with respect to each other and with respect to the incision.

3. A surgical closure as described in claim 2, wherein said bridging means comprises a strip integrally and continuously formed with said first and second surgical tape members.

4. A surgical closure as described in claim 2, wherein said bridging means comprises a removable strip that is adhesive-free at the area which contacts the skin, and further including means carried by said removable strip for aiding the operator to space said first and second surgical tape members equally from the incision.

5. A surgical closure which comprises: a first surgical tape member for application to one side of an incision; a second surgical tape member for application to the other side of the incision; and an independent belt-like tie strip for coupling said first and second surgical tape members; said first surgical tape member carrying a tie strip anchor comprising a hollowed member for holding said tie strip, said second surgical tape member carrying a tie strip slide, said tie strip having a toothed upper surface to form a ratchet, and said tie strip slide including a pawl for engaging said ratchet during sliding of said tie strip when the incision is being closed; said pawl being spaced, from the surface on which the tie strip lies, a distance that is smaller than the thickness of the tie strip; and further including a plurality of said surgical closures in a connected assembly, said connected assembly comprising tear strip means separating each surgical closure.

6. A surgical closure which comprises: a first surgical tape member for application to one side of an incision; a second surgical tape member for application to the other side of the incision; said first surgical tape member carrying a tie strip anchor and said second surgical tape member carrying a tie strip slide, said tie strip slide including a locking member; and a tie strip coupling said first and second surgical tape members, said anchor comprising a hollow, rectilinear member for holding a belt-like tie strip, and said tie strip slide including a pair of parallel side members for restraining said tie strip from lateral movement and a cross member bridging said side members for restraining said tie strip from upward movement; at least a portion of said locking member being spaced, from the surface on which the tie strip lies, a distance that is smaller than the thickness of the tie strip, whereby said locking member cooperates with said tie strip to maintain said tie strip within said tie strip slide.

7. A surgical closure which comprises: a first surgical tape member for application to one side of an incision; a second surgical tape member for application to the other side of the incision; and an independent belt-like tie strip coupling said first and second surgical tape members; said first surgical tape member carrying a tie strip anchor comprising a hollowed member for holding said tie strip, said second surgical tape member carrying a tie strip slide, said tie strip having a toothed upper surface to form a ratchet, and said tie strip slide including a pawl for engaging said ratchet during sliding of said tie strip when the incision is being closed, said tie strip slide including a pair of parallel side members for restraining said tie strip from lateral movement, a pair of upper cross members bridging said side members for restraining said tie strip from upward movement, and a pair of lower cross members aiding to hold said tie strip firmly against said pawl with one of said upper cross members cooperating with one of said lower cross members to force said tie strip into a generally S-shape whereby a portion of said tie strip is held against the patient's skin after application.

* * * * *